United States Patent [19]

Kanshin et al.

[11] Patent Number: 4,476,863
[45] Date of Patent: Oct. 16, 1984

[54] SURGICAL INSTRUMENT FOR ESTABLISHING CIRCULAR COLOANASTOMOSES

[76] Inventors: Nikolai N. Kanshin, Malaya Filevskaya ulitsa, 68, kv. 10; Igor A. Guskov, ulitsa Metallurgov, 28, kv. 176; Alexei A. Konoplev, shosse Entuziastov, 68, kv. 47; Alexandr E. Sachkov, ulitsa Molostovykh, 15, korpus 2, kv. 97; Matvei M. Mats, Veshnya-kovskaya ulitsa, 25/2, kv. 412, all of Moscow, U.S.S.R.

[21] Appl. No.: 253,523

[22] Filed: Mar. 9, 1981

[51] Int. Cl.³ .............................................. A61B 17/11
[52] U.S. Cl. ................... 128/305; 128/334 R; 128/334 C; 227/19; 227/DIG. 1
[58] Field of Search ............... 128/334 R, 334 C, 305, 128/330; 227/19, DIG. 1; 411/544, 347

[56] References Cited

U.S. PATENT DOCUMENTS

| | | | |
|---|---|---|---|
| 2,235,530 | 3/1941 | Mercer | 411/347 |
| 3,254,650 | 6/1966 | Collito | 128/334 C |
| 3,552,626 | 1/1971 | Astafiev et al. | 128/334 C X |
| 4,060,089 | 11/1977 | Noiles | 128/334 C X |

FOREIGN PATENT DOCUMENTS

| | | | |
|---|---|---|---|
| 357306 | 8/1922 | Fed. Rep. of Germany | 128/334 C |
| 264612 | | U.S.S.R. | |
| 571254 | | U.S.S.R. | |

OTHER PUBLICATIONS

Collection of papers "Iskurstuennye organi e bioupranliemye Protezy, "published 1972, "Znanie" publishers (Moscow) V. I. Shumakov "Iskurstennye, Organy,"

Primary Examiner—Michael H. Thaler
Attorney, Agent, or Firm—Lilling & Greenspan

[57] ABSTRACT

The surgical instrument of the present invention is for establishing circular anastomoses between various segments of the colon.

The surgical instrument comprises a cylindrical body having a mandrel 2 at one of its ends and accommodating a coaxially arranged rod 3 carrying a circular knife 4 locked in place thereon and provided with a mechanism for its longitudinal traversing, and a stem 6 carrying a thrust head 7 axially traversable with respect to the rod 3, and a circular anastomosing mechanism 8, which is made up of two members. One of the members of said mechanism is located on the mandrel 2 and carries a number of suturing elements adapted to interact with the rod 3 so as to travel together with the latter when establishing circular anastomoses, while the other member is situated on the thrust head 7. The member of the circular anastomosing mechanism 8 that is located on the mandrel 2 comprises two rings 9 and 10 spaced somewhat apart from each other. A plurality of suturing elements are needles 11 equispaced circumferentially between said rings, while some of the needles 11 carry shock absorbers 12. The other member of the circular anastomosing mechanism 8 that is situated on the thrust head 7 is essentially a ring 14 so connected to the latter as to be separable therefrom when anastomosing. Both of the members of the circular anastomosing mechanism 8 are joined together through the needles 11 in the course of circular anastomosing and are left in the colonic lumen until a complete necrosis of the compressed colon portion occurs.

5 Claims, 8 Drawing Figures

SURGICAL INSTRUMENT FOR ESTABLISHING CIRCULAR COLOANASTOMOSES

FIELD OF THE INVENTION

The present invention relates to medical equipment and more specifically, to surgical instruments for establishing circular coloanastomoses.

BACKGROUND ART

One prior-art surgical instrument for establishing circular coloanastomoses is known to comprise a cylindrical body having a mandrel at one of its ends and accommodating a coaxially arranged a rod which carries a circular knife held in place thereto, and is provided with a mechanism for its longitudinal traversing, a stem carrying a thrust head, and a mechanism for establishing circular anastomoses, said mechanism consisting of two members, of which one is mounted on the mandrel and the other, on the thrust head. Clearance between the members of the aforesaid mechanism required for applying a purse-string suture is adjustable by a screw-and-nut pair provided on the stem. The mandrel-mounted member of the mechanism for establishing circular anastomoses (hereinafter termed "circular anastomosing mechanism" for the sake of brevity), comprises a cylindrical bush accommodating a splined ring fixed in position thereon so as to define staple slots together with the inner surface of the bush. A cylinder-shaped staple ejector is also accommodated inside the bush. The surface of the thrust head facing the bush carries a plurality of staple recesses equispaced circumferentially thereon so as to correspond to the staple slots and serving to impart the B-shape to the staples in the course of suturing.

The application procedure of the above-discussed known instrument comprises introducing its working components into the lumen of the colon portions being stitched together and fixing the ends of the abovesaid colon portions on the stem of the surgical instrument between the two members of the circular anastomosing mechanism by tightening up preliminarily applied purse-string sutures. Then, both members of the circular anastomosing mechanism are brought together, whereupon the staples are driven out of the slots by the staple ejector and the circular knife longitudinal traversing mechanism, with the result that the staples pierce with their pointed legs the compressed colonic walls to get into the recesses and be bent into the shape of the letter B, thus firmly uniting the ends of the colon portions to be stitched together. Then the circular knife cuts a round hole in the colon within the suture.

Once the suture has been applied, the circular knife longitudinal traversing mechanism is returned to the initial position together with the staple ejector, the bush is disengaged from the thrust head by rotating the nut of the circular knife longitudinal traversing mechanism, and the instrument is withdrawn from the colon operated upon.

The known prior-art instrument discussed above is capable of applying different-diameter circular staple sutures by being provided with a set of changeable staple bushes, ejectors and knives, whereby the instrument is applicable to different-diameter colons whatever the depth of the operative field. However, metal staples left in the bulk of the colonic wall for a prolonged period of time contribute to ingress of infection from the colonic lumen into the bulk of colonic walls being sutured, which makes its way through the holes punctured by the staples. This, in turn, might be cause an inflammatory process resulting in a cicatricial constriction of the anastomotic lumen. In addition, a staple suture involves application of a serous ligature suture along the entire perimeter of the anastomosis so as to prevent propagation of infection and inflammatory process beyond the anastomosis established, which is fraught with peritonitis. Within a late postoperative period, metal staples left in the area of the anastomosis in prolonged contact with the colonic lumen favor the onset of a cicatricial stenosis of the established colostomy. Moreover, in some cases a staple suture fails to provide reliable hemostasis.

DISCLOSURE OF THE INVENTION

The present invention is intended to provide a surgical instrument for establishing coloanastomoses incorporating a circular anastomosing mechanism featuring a constructional arrangement that makes it possible to dispense with the use of a ligature suture, to prevent any foreign body from being left in the area of the anastomosis after the tissues have been inosculated, to ensure against ingress of infection from the colonic lumen, to provide full hemostasis, to render simple and reliable establishing of an anastomosis and to reduce the operating time.

The aforesaid object of the present invention is accomplished in a surgical instrument for establishing circular anastomoses, comprising a cylindrical body having a mandrel at one of its ends and accommodating a coaxially arranged rod which carries a circular knife held in place thereto, and is provided with a mechanism for its longitudinal traversing, a stem carrying a thrust head axially traversable with respect to the rod, a mechanism for establishing circular anastomoses made up of two members of which one member is situated on the mandrel and carries a number of suturing elements adapted to interact with the rod being jointly traversed in the course of establishing circular anastomoses, while the other member of the mechanism is located on the thrust head. According to the present invention, the portion of the circular anastomosing mechanism situated on the mandrel comprises two rings spaced somewhat apart from each other and a plurality of suturing elements equispaced circumferentially between said rings and made essentially as needles, some of which have shock absorbers, whereas the other member of the circular anastomosing mechanism located on the thrust head is in fact a ring coupled to the thrust head with a possibility of being separated therefrom in the course of anastomosing, both of the members of the circular anastomosing mechanism being joined together through said needles in the course of anastomosing and being left in the colonic lumen until complete necrosis of the compressed colon portion occurs.

The constructional arrangement of the circular anastomosing mechanism provides for a firm union of the colonic portions being sutured with an adequate area of serous membranes. Compression of the colonic wall portions through which the needles are to pass defines reliable hemostasis and prevents ingress of infection from the colonic lumen both in between the compressed colonic walls and along the needles, whereby heating proceeds with a minimized inflammatory reaction within the area of the anastomosis and application of ligature serous sutures along the entire perimeter of the anastomosis can be dispensed with. After the circular anastomosing mechanism has been expelled from patient's organism no foreign bodies are left within the area of the anastomosis. Thus, the factor causative of inflammatory reaction in the anastomosis is eliminated. In addition, the intestinal tissues are compressed gradually regardless of their thickness due to the provision of shock absorbers.

It is quite reasonable that the ring provided on the thrust head be made from a biologically inert polymer material and that at least three needles have annular recesses to engage with said ring, while the thrust head diameter be somewhat smaller than the diameter of the circular knife for said head to pass when withdrawing the instrument from the colon through said ring after the latter has been cut through by the circular knife.

This makes it possible to strongly lock the two members of the circular anastomosing mechanism against each other. In addition, the ring is in fact a support for the needles, and being made from a polymer material enables the ring to be cut off by the circular knife for a complete and free withdrawal of every component of the surgical instrument from patient's organism.

Fluorinated plastic may be used as a biologically inert polymer material.

It is expedient that, with a view to preparing the colon distal end for anastomosing, the surgical instrument be provided with a spool fittable over the stem having an annular ridge for the spool to rest upon, said annular ridge being spaced apart from the thrust head for a distance that is required for the purse-string suture to be drawn tight on the colon proximal end against the stem.

This makes it possible to do away with application of a purse-string suture to the colon distal end (which in some cases proves to be impracticable deeply in the small pelvis) thereby rendering the operation more aseptic. In addition, when bringing together both members of the circular anastomosing mechanism, the tissues fixed on the spool are pulled together with the latter into the circular interior, thus forming a cone-shaped space, wherein there are freely accommodated the tissues of the other colon end fixed on the stem of the surgical instrument.

It is quite reasonable that the surgical instrument be provided with a device for positioning the spool in the colonic lumen, said device comprising a setting rod, which carries two fixing elements spaced somewhat apart from each other and held by virtue of a threaded joint, said elements being shaped as two cone frustums arranged against each other and facing each other with their lesser bases, while the spool is interposed between said elements on said setting rod. One of the fixing elements is mounted at one of the setting rod ends, while the other fixing element distant to the end of the setting rod has an axial hollow space for the spool to accommodate.

Practical application of the aforesaid device in the operation enables one to accurately and purposefully fix the distal colon end on the spool when placing a ligature upon said end.

BRIEF DESCRIPTION OF THE DRAWINGS

To promote understanding an exemplary embodiment of the present invention will hereinafter be described in detail with reference to the accompanying drawings, wherein:

FIG. 3 is a longitudinal-section view facing arrow A in FIG. 1;

BEST MODE OF CARRYING OUT THE INVENTION

Figure 1:
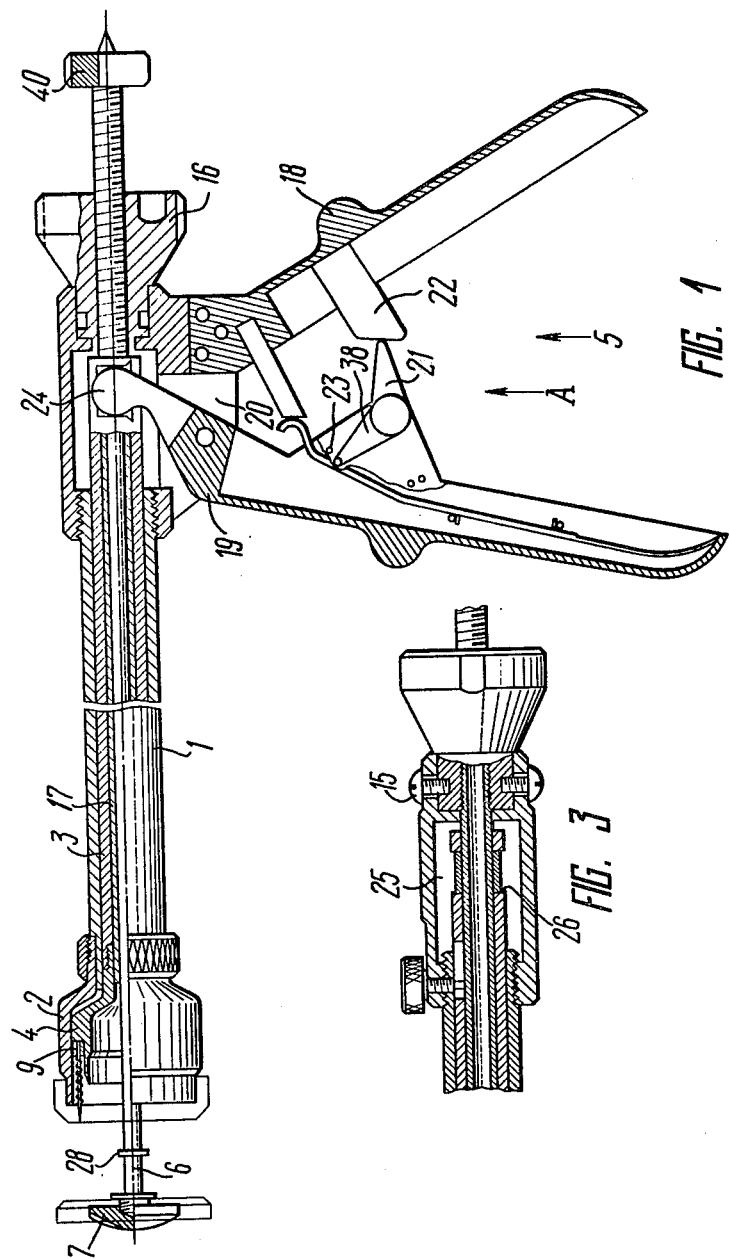
FIG. 1 is a general diagrammatic view of a surgical instrument for establishing coloanastomoses, according to the present invention.

The surgical instrument for establishing circular coloanastomoses incorporates a cylindrical body 1 (FIG. 1) carrying a mandrel 2 at one of its ends. Arranged coaxially in the cylindrical body 1 are a rod 3 carrying a circular knife 4 held in place thereto and having a mechanism 5 for traversing the rod longitudinally and a stem 6 carrying a thrust head 7, which is axially traversable with respect to the rod 3. The surgical instrument is provided with a mechanism 8 (FIG. 2) for establishing circular anastomoses, which is made up of two members. One of the members of the mechanism 8 is situated on the mandrel 2 and comprises two rings 9 and 10 spaced somewhat apart from each other. A plurality of suturing elements are equispaced circumferentially between the rings 9 and 10, said elements being in fact needles 11 locked-in with the ring 9. Some of the needles 11 have shock absorbers 12, while at least three needles 11 have annular recesses 13. The other member of the circular anastomosing mechanism 8 is arranged on the thrust head 7 and is essentially a ring 14 made from a biologically inert polymer material, which enables said ring 14 to be separated from the thrust head 7 during inosculation by being cut through by the knife 4. Used as a biologically inert polymer material may be fluorinated plastic (fluoroplast). Both of the members of the circular anastomosing mechanism 8 are joined together through the needles 11 when placing circular anastomoses, and are left in the colonic lumen until the compressed necrotic colon portion is cast off. The thrust head 7 is shaped as a nut having a diameter somewhat smaller than the diameter of the circular knife 4, so that the thrust head 7 be free to pass through the plastics ring 14 after its having been cut through by the circular knife for the surgical instrument to be withdrawn from the colon operated upon.

A nut 16 (FIG. 1) is held to the end face of the cylindrical body 1 by screws 15 (FIG. 3), said nut being adapted to engage the threaded portion of a stem 17 and cause the latter to traverse along the cylindrical body 1, with the result that both of the members of the circular anastomosing mechanism 8 (FIG. 1) can be either brought together or set apart.

The mechanism 5 (FIG. 1) for longitudinal traversing of the circular knife 4 comprises a stationary handle 18 and an articulately movable handle 19, both of them being fixed in place on arms 20 of the cylindrical body 1. The articulately movable handle 19 carries a swivel lock 21 adapted to interact with a stop 22 held in position to the stationary handle 18, the angle of swivel of the lock 21 being restricted by pins 23.

A shorter working arm 24 of the movable handle 19 enters into the interior of the cylindrical body 1 through an opening 25 so as to straddle the flat side surfaces of the rod 3. Shoulders 26 are provided in the rod 3, serving as stops for the arm 24.

Figure 4:
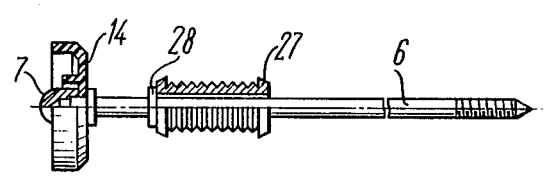
FIG. 4 is the setting rod and spool assembly.

In order to prepare the colon distal end for anastomosing, the surgical instrument is provided with a spool 27 (FIG. 4) fittable over the stem 6, which has an annular ridge 28 for the spool 27 to rest upon, said annular ridge 28 being spaced apart from the thrust head 7 for a distance that is long enough for the purse-string suture applied to the colon distal end to be drawn tight on the stem 6.

Figure 5:
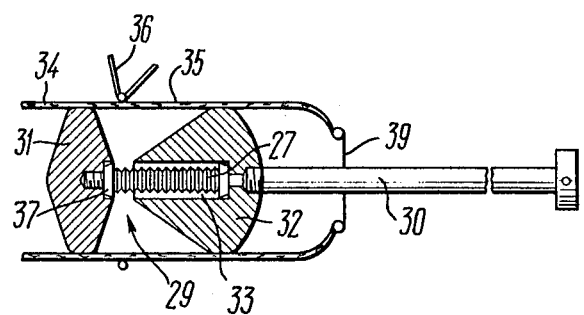
FIG. 5 is a device for positioning the spool in the rectum, shown when introduced into the rectal lumen.

The surgical instrument has a device 29 (FIG. 5) for the spool 27 to set in position in the colonic lumen, said device 29 comprising a setting rod 30, which carries two fixing elements 31 and 32 spaced somewhat apart from each other and held by virtue of a threaded joint. The fixing elements 31 and 32 are shaped as oppositely arranged cone frustums facing each other with their lesser bases, while the spool 27 is interposed therebetween. The fixing element 31 is located at one end of the setting rod 30, while the fixing element 32 distant to the end of the setting rod 30 has an axial hollow space 33 for the spool 27 to accommodate.

The herein-proposed surgical instrument for establishing circular coloanastomoses is applicable for anastomosing by the end-to-end and end-to-side techniques, as well as for inosculating various colon segments or establishing entercolostomies. Considered hereinbelow is an exemplary anastomosing operation by the end-to-end technique.

Figure 2:
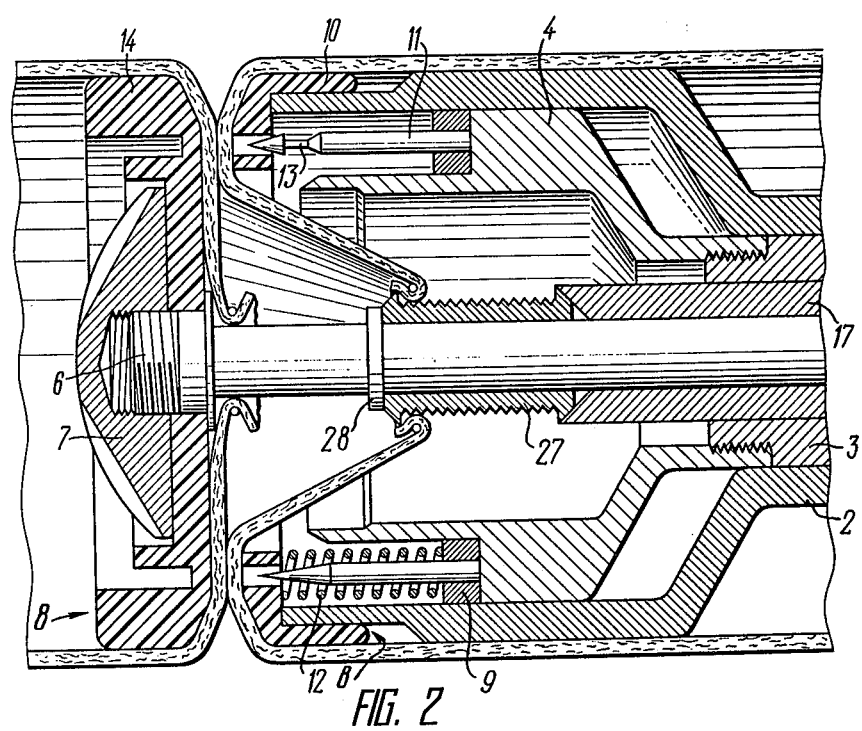
FIG. 2 is a scaled-up view of a mechanism for establishing circular anastomoses, shown before the instance of suturing.
Figure 6:
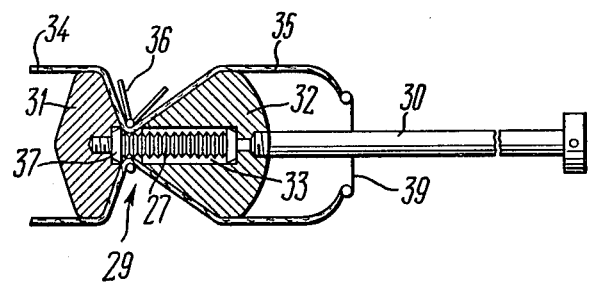
FIG. 6 illustrates the position of the rectal walls after the thread has been drawn tight and ties up on the spool.
Figure 7:
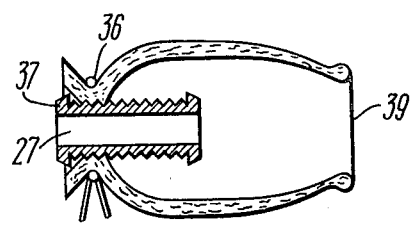
FIG. 7 is a view of the rectum after its having been severed.
Figure 8:
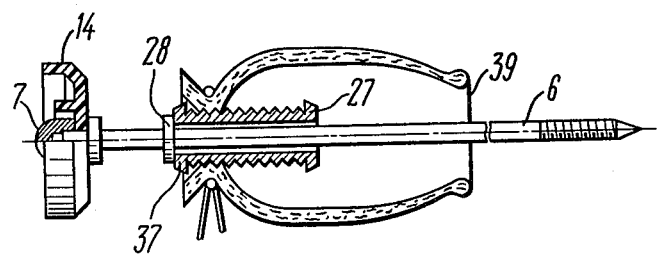
FIG. 8 is a view of the rectum with the stem of the surgical instrument introduced into the spool.

In order to fix the end of the severed rectum so as to establish an end-to-end rectocolostomy prior to ablating the pathologically affected rectal segment, the spool 27 (FIG. 6) is introduced into the rectum via the anus using the device 29. Having brought the spool 27 along with the device 29 short of an affected rectal segment 34, one must bind up the spool together with an unaffected rectal segment 35, using a thread 36, whereupon the thread is tied up into a knot at a flange 37 of the spool 27. Then one must back out the fixing element 32 using the setting rod 30 and next bring the latter together with the fixing element 32 out of the rectal lumen, after which one must tension the rectum and sever it at the flange 37 (FIG. 7) of the spool 27. Thereupon the affected portion of the rectum is removed together with the fixing element 31 accommodated therein. Next the stem 6 (FIG. 8) carrying the plastic ring 14 and the thrust head 7 is introduced into the bore of the spool 27 until the flange 37 of the latter rests against the annular ridge 28. Thus, the end of the severed rectum is fixed on the stem 6 of the surgical instrument in a quick and simple way. Further the surgical instrument is introduced into the anus 39 along the stem 6 and is fixed exactly in the working position on the stem 6 by the annular ridge 28, the spool 27 and a nut 40 (FIG. 1). The distance from the annular ridge 28 to the plastic ring 14 is large enough to freely fix the proximal segment of the rectum on the stem 6 under the thrust head 7 and the plastic ring 14. This done one must rotate the nut 16 to bring together the both members of the circular anastomosing mechanism 8 until they assume the working position, whereupon one must turn the handle 38 of the lock 21 so as to disengage it from the stop 22 and remove as far as possible therefrom, and must press the movable handle 19. As a result, the shorter actuating arm 24 of the handle presses the shoulders 26 of the rod 3, thus causing the latter to traverse together with the circular knife held thereto. The knife 4, in turn, moves the ring 9 together with the needles 11 fixed thereon. Thus, the ring 9 with the needles 11 finally locks together both of the members of the circular anastomosing mechanism 8, while some of the needles 11, which have the annular recesses 13 pass through the plastic ring 14 to tightly press the latter against the ring 10 and fix it thereon.

The circular knife cuts off the surplus of the intestinal walls, which are then removed when withdrawing the surgical instrument together with the thrust head 7 locked thereto, through the anal orifice. Removed together with the thrust head 7 are also the pieces of the plastic ring 14 cut off by the circular knife 4.

The circular anastomosing mechanism 8 is left in the rectal lumen until the necrotized portion of the rectum is rejected; it is removed from patient's organism by natural way 7 to 10 days after the operation.

We claim:

1. A surgical instrument for establishing circular coloanastomoses in a colonic lumen, comprising a cylindrical body having a mandrel at one end, a rod coaxially arranged in said mandrel and having a longitudinal axis, a circular knife attached to said rod, means for moving said rod along its longitudinal axis, a stem having a thrust head axially movable with respect to said rod, means for establishing circular anastomoses comprising two members, one said member located on said mandrel, a plurality of suturing elements attached to said one member adapted to move with the rod during the course of establishing circular anastomoses, the other said member located on the thrust head, wherein a portion of said circular anastomosing means located on said mandrel comprises two rings spaced apart from each other, said plurality of suturing elements equispaced circumferentially between said rings, said suturing elements comprising needles, shock absorbing means accommodated on at least one of said needles, and wherein the other said member of said circular anastomosing means comprises a third ring coupled to the thrust head and adapted to separate therefrom during the course of anastomosing, both of the members of said circular anastomosing means being joined together through said needles in the course of anastomosing and are adapted to remove in the colonic lumen until complete necrosis of a compressed colon portion occurs.

2. The surgical instrument of claim 1, wherein said third ring coupled to the thrust head, comprises a biologically inert polymer material, and at least three of said needles have annular recesses to engage with said third ring, while the thrust head diameter is smaller than the diameter of the circular knife.

3. The surgical instrument of claim 2, wherein the biologically inert polymer material comprises a fluorinated plastic.

4. The surgical instrument of claim 1, also provided with a spool which fits over said stem, said stem having an annular ridge for the spool to rest upon, said annular ridge being spaced apart from the thrust head.

5. The surgical instrument of claim 4, with means to place the spool in the colonic lumen, said means comprising a setting rod, two fixing elements attached to said setting rod, said fitting elements spaced apart from each other and held by a threaded joint, said fixing elements having the shape of two cone frustums arranged opposite each other, said cone frustums facing each other with their lesser bases, with the spool interposed between said fixing elements on the setting rod, one fixing element being mounted at one of the setting rod ends, while the other fixing element being mounted away from the end of the setting rod, said other fixing element having an axial opening adapted to accommodate said spool.

* * * * *